United States Patent [19]

Sperl et al.

[11] Patent Number: 4,795,708
[45] Date of Patent: Jan. 3, 1989

[54] NOVEL BACKTERIA AND SINGLE CELL PROTEIN PRODUCTION THEREWITH

[75] Inventors: George T. Sperl, Grayslake, Ill.; John A. Cruze, Bartlesville, Okla.

[73] Assignee: Phillips Petroleum Company, Bartlesville, Okla.

[21] Appl. No.: 838,064

[22] Filed: Mar. 10, 1986

[51] Int. Cl.[4] .......................... C12N 1/32; C12N 1/34; C12N 1/20

[52] U.S. Cl. .................................. 435/246; 435/804; 435/858; 435/252.1

[58] Field of Search ............... 435/247, 253, 804, 858, 435/246, 68

[56] References Cited

U.S. PATENT DOCUMENTS

| Re. 30,543 | 3/1981 | Hitzman et al. | 435/246 |
|---|---|---|---|
| 3,647,632 | 3/1972 | Johnson et al. | 195/142 |
| 3,981,774 | 9/1976 | Hitzman | 195/49 |
| 3,982,998 | 9/1976 | Hitzman et al. | 195/49 |
| 3,994,781 | 11/1976 | Haggstrom | 195/49 |
| 4,048,013 | 9/1977 | Wagner et al. | 435/247 X |
| 4,062,727 | 12/1977 | Srinivasan et al. | 195/28 R |
| 4,106,988 | 8/1978 | Ohsugi et al. | 195/49 |
| 4,282,328 | 8/1981 | Fukuda et al. | 435/255 |
| 4,284,724 | 8/1981 | Fukuda et al. | 435/255 |
| 4,414,329 | 11/1983 | Wegner | 435/68 |

OTHER PUBLICATIONS

Hirt et al., "Formaldehyde Incorporation by a New Methylotroph (L3)", *Applied and Environmental Microbiology*, Jul., 1978, pp. 56–62.

Primary Examiner—Thomas G. Wiseman
Assistant Examiner—Charles L. Patterson, Jr.
Attorney, Agent, or Firm—J. E. Phillips

[57] ABSTRACT

Single cell protein (SCP) is produced at high yields from a novel methanol assimilating *Methylomonas sp.* grown at elevated temperatures in an aerobic bacterial fermentation process.

18 Claims, No Drawings

NOVEL BACKTERIA AND SINGLE CELL PROTEIN PRODUCTION THEREWITH

This invention relates to a novel methanol assimilating bacterium and to high yield, high temperature processes for the production of single cell protein by bacteria.

BACKGROUND OF THE INVENTION

Much effort has been expended to develop various fermentation processes in which single cell protein (SCP) is obtained and/or various chemical conversions are achieved by the growth of a variety of microorganisms on various carbon-containing substrates. The SCP product is useful as a protein food-source, while chemical conversions offer sources of new chemicals such as bio-polymers, pharmaceuticals, and enzymes, even commodity chemicals. In addition, genetically modified organisms can be employed to produce valuable polypeptide products.

The carbon energy substrates employed for the growth of microorganisms should be relatively cheap, readily available, and preferably water-soluble. Initially, hydrocarbons were considered as carbon energy sources for SCP. However, oxygenated hydrocarbons, such as alcohols and sugars, are more preferred as sole or partial substrates due to their relative water-solubility in an aqueous ferment, and in the reduced molecular oxygen requirements for microbial conversion-growth processes.

A limiting factor in efforts to commercialize various fermentation processes has been the cost of feedstock, cost of utilities, equipment costs and the like. Desired, therefore, is a microorganism which utilizes inexpensive feedstocks and is capable of producing single cell protein products in high yield, at relatively high growth temperatures. Such an organism would allow for the production of single cell protein material with reduced feedstock costs, as well as reduced equipment and operating costs.

OBJECTS OF THE INVENTION

An object of the present invention, therefore, is a novel bacterium which is capable of producing single cell protein material from inexpensive feedstocks in high yield.

Another object of the present invention is a novel bacterium which is capable of producing single cell protein material at relatively high fermentation temperatures.

These and other objects of the invention will become apparent from inspection of the detailed description and appended claims provided herewith.

STATEMENT OF THE INVENTION

In accordance with the present invention, we have discovered a novel methanol assimilating bacterium which is capable of growth at relatively high fermentation temperatures to high yields on relatively inexpensive carbon sources. The novel bacterium of the present invention makes possible the efficient production of bacterial single cell protein material from inexpensive feedstocks.

Heretofore, continuous processes for the production of bacterial single cell protein material from methanol typically gave low bacterial cell yields, i.e., less than 40 grams of cells per grams of feedstock when grown at temperatures in excess of 30° C. Our invention, however, provides a novel methanol assimilating bacterium capable of producing upon fermentation bacterial cells in high yield, i.e., yields in excess of 40 grams of cells per grams of feedstock (g/g). The high yields of bacterial cells obtained at the elevated temperatures employed in the practice of the present invention mean more efficient production of biomass and related cellular products, especially when cells are produced under continuous fermentation conditions.

Yield is defined as the amount of cells by weight produced for a given consumption by weight of carbon energy source or substrate fed to the fermentor, and is usually expressed as grams/gram, (i.e., grams of cells produced per gram of substrate feed). While yield is sometimes reported in terms of dried ferment per liter of aqueous ferment, preferably, yield should be reported in terms of washed, dried cells per liter of aqueous ferment, which is more accurate. In our specification, yield is always reported as washed, dried cells per liter of aqueous ferment, unless otherwise specified.

DETAILED DESCRIPTION OF THE INVENTION

In accordance with the present invention, a novel methanol assimilating bacterium is provided which is capable of growth at temperatures in excess of 30° C. under substantially continuous aerobic aqueous fermentation conditions on a suitable non-hydrocarbon substrate, employing oxygen, an assimilable-nitrogen source, and a high input of defined ratios of nutrient mineral salts, to efficiently produce single cell protein material.

It is indeed surprising, in our experience, to achieve such high yields of cellular products at such high fermentation temperatures with a bacterium which is suitable for use as single cell protein material. The high yields achievable by the practice of our invention are typically in excess of about 40 g/g.

The novel methanol assimilating bacterium of the present invention was isolated from Caney River sediment at Johnstone Park in Bartlesville, Okla. Enrichment cultures using 0.5 weight percent methanol as a carbon source yielded a bacterium which has been given the laboratory designation 31A, and assigned the accession number NRRL B-15740.

The designation NRRL B-15740 reflects the fact that the bacterial culture 31A has been deposited with an official depository, the United States Department of Agriculture, Agricultural Research Service, Northern Regional Research Laboratory, Peoria, Ill. 61604. The deposit has been made in accordance with the Patent and Trademark Office practice such that all restrictions on availability of the strain to the public will be irrevocably removed upon granting of a patent on this application, of which this important strain is the subject. Thus, this strain will be available to the public for utilization in accordance with our invention.

The strain 31A (NRRL B-15740) has been further characterized as follows:

| Treatment | Observation |
| --- | --- |
| Growth on methanol-containing agar plates at pH 6.0. | Circular white colonies about 2-3 microns in diameter are apparent after 3 days incubation at 37° C. |
| Growth on nutrient agar | No growth after 3 days |

| Treatment | Observation |
| --- | --- |
| plates at pH 6.8. Cultivation on methanol-agar plates for 3 days at 37° C. | incubation at 37° C. Morphology: (a) rod-shaped, 0.4 microns × 2.0 microns; (b) cells are gram negative; (c) no spores were observed; and (d) cells were non-motile. |
| pH profile in methanol-containing media. | Optimum pH about 6.0–7.0; no growth at pH 4.0 or less or at pH 9.0 or greater. |
| Utilization of inorganic nitrogen as nitrogen source. | Both ammonium and nitrate salts are utilized as nitrogen source. |
| Utilization of methylamine as carbon and energy source. | Positive. |
| Ability to convert L-hydroxypyruvate to D-glycerate. | Negative during growth on methanol; thus 31A does not have a serine metabolic pathway. |
| Ability to convert dihydroxyacetone to dihydroxyacetone phosphate. | Negative during growth on methanol; thus 31A does not have a xylulose monophosphate pathway. |
| Ability to convert formaldehyde and ribulose-5-phosphate to a hexulose-6-phosphate (i.e., a 6-carbon sugar phosphate). | Positive during growth on methanol; thus 31A does have a ribulose monophosphate pathway. |

On the basis of the above information, strain 31A is believed to be a *Methylomonas species*, and is sometimes referred to as such in this specification.

Culturing of the novel bacterium of the present invention is accomplished in a growth medium comprising an aqueous mineral salts medium, a suitable non-hydrocarbon substrate as the carbon energy source material, molecular oxygen, an assimilable-nitrogen source, and of course, a starting inoculum of the *Methylomonas species* 31A.

It is necessary to supply suitable amounts of selected mineral nutrients in proper proportions in the feed media in order to assure proper bacterial growth, to maximize assimilation of the carbon energy source by the cells in the microbial conversion process, and to achieve maximum cellular yields with maximum productivity and cell density in the aqueous fermentation media.

Although the composition of the aqueous ferment can vary over a wide range, depending in part on the substrate employed, in accordance with our invention, the minerals content in the ferment, i.e., liquid plus cells, can be relatively high. Indeed, in the practice of one embodiment of the present invention, i.e., where cells are grown to high cell density, the minerals content in the ferment is maintained at higher levels than heretofore considered suitable by the prior art for bacterial fermentations.

For purposes of this disclosure, cell density is defined as the concentration of cells by weight on a dry basis per volume of ferment. The ferment is defined as the total ungased liquid volume of aqueous fermentation broth or liquor, including cells. Cell density usually is expressed as grams/liter.

In accordance with another embodiment of the present invention, the *Methylomonas species* 31A can be grown under standard fermentation conditions well known to those of skill in the art to cell densities in the range of about 20–40 g/L.

Growth of the *Methylomonas species* 31A to cell densities in the range of 20–40 g/L provides high yield conversion of the feed carbon and energy source to cell mass and, at the same time, allows for efficient growth of the bacterium at fermentation temperatures as high as 37° C. without the generation of excessive quantities of heat which removal presents a difficult engineering problem.

Set forth in Table I below are the minimum, (i.e., broad), preferred and presently most preferred ranges of concentrations of the various elements required to be in the aqueous ferment when *Methylomonas species* 31A is to be grown to high cell densities. The concentration in each instance is expressed as of the element, though it is recognized that all or part of each can be present in the form of a soluble ion, such as where P is present in a combined form, such as the phosphate. The amount of each element is expressed in grams or milligrams of element per liter of ferment (aqueous phase, including cells):

TABLE I

| Element, Units | Weight of Element per Liter of Ferment | | |
| --- | --- | --- | --- |
| | Broad Range | Preferred Range | Most Preferred |
| P, g | 1.3–6.5 | 2.0–5.0 | 2.5–4.0 |
| K, g | 1.0–4.0 | 1.3–3.5 | 2.0–3.0 |
| Mg, g | 0.4–1.6 | 0.5–1.3 | 0.6–1.0 |
| Ca, g | 0.1–0.7 | 0.13–0.5 | 0.2–0.3 |
| S, g | 0.5–2.6 | 0.7–2.3 | 0.7–2.1 |
| Fe, mg | 10–80 | 25–65 | 25–50 |
| Zn, mg | 5–65 | 10–50 | 20–40 |
| Cu, mg | 1–5 | 1.5–3 | 1.7–2.6 |
| Mn, mg | 1–65 | 2.6–40 | 4–15 |
| Mo, mg | 0.2–10 | 0.5–8 | 0.8–3 |
| Co, mg | 0.1–0.7 | 0.1–0.5 | 0.2–0.4 |
| B, mg | 0.05–0.4 | 0.09–0.35 | 0.1–0.26 |

Sulfur desirably is employed in the form of sulfate. Some of the metals required are advantageously added in the form of a sulfate. Thus, the minimum concentrations of sulfur normally are exceeded. Preferably, magnesium, calcium, iron, zinc, copper, manganese and cobalt are employed in the form of a sulfate, or in the form of a compound which is converted in-situ to a sulfate. Preferably, molybdenum and boron are employed in a soluble form such as, for example, the molybdate and borate, respectively. Potassium preferably is employed as a sulfate or phosphate, or in the form of a compound which is converted in-situ to a sulfate or phosphate. The phosphorus preferably is employed in the form of phosphoric acid or in the form of a phosphate, monohydrogen phosphate, or dihydrogen phosphate, e.g., as a potassium or ammonium salt, or as a compound which is converted in-situ to such a salt. While nitrogen is also required for the production of cell mass, no minimum required levels are set forth above because such minimum values are readily exceeded when a nitrogen-containing compound is used as a means to control the pH of the fermentation. As described in greater detail below, nitrogen-containing compounds such as ammonia are useful for the dual purpose of pH control and as a source of assimilable nitrogen for the proliferating cells.

Conveniently, a primary mineral salts medium can be employed to include nutrients comprising P, K, Mg, S, and Ca; and a trace mineral medium to supply nutrients comprising Fe, Zn, Mn, Mo, Co, B and Cu.

Other elements which may be present, at least in trace amounts, include such as sodium, e.g., as a sulfate; selenium, e.g., as selenite or selenate; and iodine, e.g., as iodide.

SUBSTRATE

In our high yield bacterial fermentations, the carbon-containing substrate is selected from the group consisting of methanol, methylamine and glucose. Presently preferred is methanol.

In addition to the above described carbon and energy sources, intermediates in the fermentation of $C_1$ compounds, such as, for example, formaldehyde and formate, can be added to the feed stream as yield enhancers. These yield enhancers are utilized by the growing organisms as energy source and can be added in any amount which is not toxic to the growing organism. Thus, for example, formaldehyde can be employed in amounts up to about 10 volume % of the feed carbon and energy source.

FERMENTATION CONDITIONS

Those of skill in the art can readily determine suitable fermentation conditions for the growth of *Methylomonas species* 31A at normal cell densities of 20–40 g/L. Alternatively, the novel bacterium of our invention can be grown to high cell densities as further described below.

When our *Methylomonas species* 31A is grown to high cell density, mineral salts are added at relatively high levels in the aqueous liquor, resulting in a continuous fermentation process at relatively high productivities, producing high bacterial cell densities, with high yields of bacterial cells.

In the high cell density bacterial fermentation, the aqueous ferment comprises about one-half supernatant, i.e., cell-free liquid, and one-half bacterial cells, by volume. These one-half by volume bacteria cells, however, will contain at least about two-thirds of the mineral salts content of the ferment.

The salts in the supernatant are at a relatively low concentration, since there is a high take-up by the growing reproducing cells. The mineral salts in the cells may not be as fed or applied since some may be in a bound organic form. Mineral analysis of the aqueous ferment, of course, would reflect a total mineral content.

The fermentation is an aerobic process requiring molecular oxygen which is supplied by a molecular oxygen-containing gas such as air, oxygen-enriched air, or substantially pure molecular oxygen, so as to maintain the ferment with an oxygen partial pressure effective to assist the bacteria in growing and in biochemically converting substrate in a thriving fashion.

The rate at which molecular oxygen is fed to the ferment should be such that the growth of the bacteria is not limited by lack of oxygen. Fermentor designs vary widely in their ability to transfer oxygen to the culture. Preferably, fermentation apparatus capable of providing an oxygen transfer rate of at least about 600 mmol $O_2$/L/hr will be employed, to ensure that lack of oxygen is not a problem when cells are grown to high productivity and/or high cell density.

The type of fermentor employed in the practice of our invention is not critical, though presently preferred is operation in a foam-filled fermentor. A fermentor designed to encourage and maintain the produced foam usually is beneficial to the process of achieving the increased oxygen transfer necessary to maintain desired high cell densities and rapid growth rates.

Although the overall aeration rates can vary over a considerable range, with fermentors that are efficient in oxygen transfer, aeration generally is conducted at a rate of about 0.5 to 8, preferably about 1 to 6, volumes (at the pressure employed and at 25° C.) of molecular oxygen-containing gas per liquid volume in the fermentor per minute. This amount is based on air of normal oxygen content being supplied to the reactor, so that in terms of pure molecular oxygen the respective ranges would be about 0.1 to 1.7, or preferably about 0.2 to 1.3, volumes (at the pressure employed and at 25° C.) of molecular oxygen per liquid volume in the fermentor per minute.

The pressure employed for the microbial fermentation step can range widely. Typical pressures employed are about 0 to 150 psig, presently pressures in the range of about 0 to 60 psig are preferred, more preferably pressures in the range of 35 to 40 psig are employed. At such preferred pressures a reasonable balance of equipment and operating costs versus oxygen solubility is achieved. Greater than atmospheric pressures are advantageous in that increased dissolved oxygen concentration in the aqueous ferment is obtained, which in turn increases cellular growth rates. This is counterbalanced, however, by the fact that high pressures increase equipment and operating costs.

The fermentation temperature can vary somewhat, but generally will be in the range of about 25° C. to 42° C., presently preferred about 30° to 42° C. The most preferred temperatures are those in excess of 30° C. because of the excellent growth characteristics of 31A at such temperatures.

Bacteria require a source of assimilable nitrogen. The assimilable nitrogen can be supplied by any nitrogen-containing compound or compounds capable of releasing nitrogen in a form suitable for metabolic utilization by the microorganism. While a variety of organic nitrogen source compounds, such as protein hydrolysates, technically can be employed, usually cheaper nitrogen-containing compounds such as ammonia, ammonium hydroxide, urea, and various ammonium salts such as ammonium phosphate, ammonium sulfate, ammonium pyrophosphate, and ammonium chloride can be utilized. Ammonia gas itself is convenient for large scale operations, and can be employed by bubbling through the aqueous microbial ferment in suitable amounts. At the same time, ammonia can be used to assist in pH control.

The pH range in the aqueous microbial ferment should generally be maintained in the range of about 5 to 8, preferably about 6 to 7.5. Preferences for a certain pH range are dependent to some extent on the medium employed, and thus may change somewhat with change in medium as can be readily determined by those skilled in the art.

The average retention time of the aqueous ferment in the fermentor can vary considerably, depending in part on the fermentation temperature and oxygen availability. Generally, the retention time will vary in the range of about 1 to 20 hours, presently preferably about 2 to 8 hours, based on average retention.

High concentrations of certain substrates may be inhibitory to satisfactory bacterial growth, or even toxic to the microorganisms in the fermentation. Relatively high concentrations of such substrates as methanol thus should be avoided, so that it is generally desirable to maintain the methanol concentration in the ferment at a maximum tolerable level. This level in the ferment generally is within the range of about 0.005 to 1 volume percent, preferably about 0.003 to 0.01 volume percent.

Conveniently, the fermentation is conducted in such a manner that the substrate is controlled as a limiting factor, providing good conversion of the substrate to bacterial cells and extracellular products, and avoiding loss of unconverted substrate.

Continuous operation is preferred for ease of control, production of uniform quantities of cells or extracellular products, and most economical uses of all equipment. In a continuous process, the substrate, aqueous mineral medium, assimilable nitrogen source, and molecular oxygen-containing gases are added continuously to the ferment in the fermentor combined with continuous withdrawal of ferment. Although the volume ratio of added carbon energy substrate to aqueous mineral medium can vary over a wide range, depending in part on the nature of the carbon-containing substrate, generally it will be in the range of about 1:9 to 6:4, presently and preferably in the range of about 2:8 to 5:5.

One skilled in the art readily recognizes that the maximum bacterial cell density obtainable is a function of the cell yield (g of cells per g of substrate feed) and the percent substrate in the total feed to the fermentor. Total feed is the carbon substrate plus mineral media including water.

If desired, part or all of the substrate and/or part of the assimilable nitrogen source such as ammonia can be added to the aqueous mineral medium prior to passing the aqueous mineral medium to the fermentor. Most convenient in our work in high cell density bacterial fermentations has been the use of a feed containing about 30 volume percent substrate to 70 volume percent mineral salts medium.

Each of the streams introduced into the reactor preferably is controlled at a predetermined rate, or in response to a need determinable by monitoring, such as concentration in the ferment of the carbon and energy substrate, the pH, the dissolved oxygen, the cell density measurable by light transmittancy, or the like, and the oxygen or carbon dioxide in the off-gases from the fermentor. The feed rates of the various materials streams can be varied so as to obtain as rapid a cell growth rate as possible, consistent with efficient utilization of the carbon and energy source, to obtain as high a yield of bacterial cells and/or extracellular products, relative to substrate charge as possible, or to maximize the particular biochemical conversion being practiced. Thus, by the process of our invention, bacterial cells can be obtained in yields of about 45 to 55 grams per 100 of grams substrate charged, depending in part on the growth conditions employed and the particular substrate used.

All fermentation equipment, e.g., reactor, vessel or container, piping, attendant circulating or cooling devices, and the like, generally are sterilized, usually by employing steam such as at about 250° F. (121° C.) for at least about 15 minutes. The sterilized reactor is inoculated with a culture of the microorganism *Methylomonas species* 31A in the presence of all the required nutrients, including molecular oxygen, and the substrate.

In starting out a continuous fermentation, the aqueous mineral medium, suitable concentration of substrate, assimilable nitrogen source, and trace components, where desired, are sterilized. These feed materials can be heat sterilized or sterilized by filtration through a series of filters, e.g., a $0.7\mu$, $0.45\mu$ and $0.2\mu$ set of filters. The sterilized materials and the starting inoculum of the bacterial strain 31A are placed in a sterilized fermentor, and suitable flows of oxygen and the various feeds are gradually commenced. It is possible to begin at low mineral salts levels in the aqueous ferment and build up to a high mineral salts level by feeding an aqueous mineral medium having a high concentration of mineral salts to the ferment, though we normally simply add high salts medium initially to the fermentor to commence immediate operation. One skilled in the art realizes that a brief lag time will usually occur at start up before the inoculum builds up enough cells for full input of salts and substrate to be effectively utilized.

PRODUCT RECOVERY

The bacterial cells produced in accordance with the present invention can be recovered from the fermentor by conventional means, such as by flocculation, foam concentration, centrifugation or filtration.

The microbial cells can be killed, if desired, by heat or chemical means, before or after the separation of the cells from the fermentor effluent.

If desired, the concentrated cells then can be washed such as by mixing with water, and separated such as by recentrifuging, or by adding water prior to or during centrifugation to substantially free the cells of mineral medium, and the washings including the separated mineral medium then can be returned to the fermentor as water and mineral medium makeup, thus substantially reducing or avoiding waste disposal problems.

The recovered cells can be dried to produce a dried product for future use. If desired, when cells are produced at high cell density, the high cell density fermentor effluent in total can be dried to produce a whole dried product of dried bacterial cells and residual water soluble substances including salts, and this whole-dried product used as an animal feed of high protein-high salts character. For human consumption, the cells can be treated as necessary to reduce the nucleic acid, but for animal feed purposes such treatment is not presently believed to be necessary.

Extracellular products can be recovered from the substantially cell-free supernatant liquid by conventional means. The substantially cell-free supernatant can be treated, for example, with acetone or a lower alcohol such as methanol or ethanol to precipitate extracellular polymeric material. The cell-free effluent also can be treated by solvent extraction and/or base extraction to recover, if desired, other extracellular products such as pigments, vitamins, or organic acids produced during the culturing process. The cell-free effluent, with or without such intervening treatment, can be returned to the fermentor as a part of the aqueous makeup, or as a substantial or almost total part of the aqueous makeup, to avoid waste disposal problems insofar as possible.

The high cell densities obtainable by our process significantly streamline and reduce the cost of single cell protein production from bacteria. The need to concentrate the resulting single cells for use as a protein product in many instances can be sharply reduced or even eliminated. The cellular product can, if desired, be washed to remove residual unconsumed salts and extracellular products such as amino acids, biopolymers, extracellular enzymes, and the like. The washed cells can then be sent directly to a dryer means such as a spray dryer.

Requirements for water to the fermentation step thus are reduced considerably, and, importantly, there is little or no waste water requiring disposal. Alternatively, if desired, the total ferment including residual salts can be dried.

The following examples are provided in an effort to assist one skilled in the art to a further understanding of our invention, and yet not to be unduly limitative of the reasonable scope of our invention. The particular reactants, conditions, ratios, and the like, are all intended to be illustrative of our invention, and not limitative of the reasonable and suitable scope thereof.

EXAMPLE I

A 4 liter fermentor equipped for continuous fermentation with an air sparging plate, stirrer, dissolved oxygen probe, pH probe, temperature measuring means and suitable inlets for adding media, ammonia and methanol substrate and an outlet for withdrawing effluent was charged with 100 mL inoculum of the *Methylomonas sp.* bacteria strain, culture number 31A, deposited with U.S. Department of Agriculture, Agricultural Research Service, North Central Region, Northern Regional Research Center, Peoria, Ill. The culture deposit was assigned the number NRRL B-15740 by the above depository. The aqueous media initially charged to the fermentor for growing up the inoculum under batch conditions had the following composition per liter:

| | |
|---|---|
| $KH_2PO_4$ | 2.0 g |
| $K_2HPO_4$ | 3.0 g |
| $MgSO_4.7H_2O$ | 0.4 g |
| $CaCl_2.2H_2O$ | 0.04 g |
| NaCl | 0.1 g |
| $(NH_4)_2SO_4$ | 2.0 g |
| Trace metals solution | 0.05 mL |

The pH was adjusted to 6.8 and the media sterilized by autoclaving. Methanol was then added to a level of 0.4% v/v.

The trace metals solution had the following composition:

| | g/L |
|---|---|
| $CuSO_4.5H_2O$ | 5.0 |
| KI | 0.8 |
| $Na_2MoO_4.2H_2O$ | 2.0 |
| $H_3BO_3$ | 0.5 |
| $ZnSO_4.7H_2O$ | 23.0 |
| $CoCl_2.6H_2O$ | 0.5 |
| $FeSO_4.7H_2O$ | 80.5 |
| $MnSO_4.H_2O$ | 9.5 |

The media used for the continuous fermentation run which followed the batch mode growth had the composition set forth in Table II:

TABLE II

| | g/L |
|---|---|
| $H_3PO_4$ | 2.85 |
| KCl | 1.0 |
| $MgSO_4.7H_2O$ | 1.5 |
| $CaCl_2.2H_2O$ | 0.2 |
| NaCl | 0.1 |
| Trace metals solution | 1.0 mL/L |
| Methanol | 100 mL/L |

Ammonia was utilized to provide pH control as well as an assimilable source of nitrogen for the microbe.

The carbon energy source was methanol and was charged during the run as an aqueous solution of 10 v/v % methanol based on the total feed composition.

The fermentor controls were set to operate at a pH of about 6.5 and at a temperature of about 30° C. The stirrer operated at 1000 rpm.

Samples of fermentor effluent were periodically removed for analysis. A portion of the sample (about 20 mL) was evaporated to dryness to determine total solids in g/L. Another portion (about 50 mL) was centrifuged and a portion of the supernatant evaporated to dryness to determine solids content of the supernatant. The centrifuged solid phase was resuspended in about 20–25 mL tap water and centrifuged again. The resulting solid phase was dried to provide the weight of washed cells in g/L of fermentor effluent. Table III below shows operating conditions at the time indicated and the corresponding analysis results on the fermentor effluent.

TABLE III

| Time hr | Feed mL/hr | pH | Temp. °C. | Yield[a] % | Washed Cells g/L |
|---|---|---|---|---|---|
| 48 | 310 | 6.5 | 30 | 40.9 | 32.3 |
| 93 | 310 | 7.5 | 33 | 40.2 | 31.8 |
| 164 | 310 | 6.0 | 33 | 43.1 | 34.0 |
| 188 | 365 | 6.0 | 33 | 42.8 | 33.8 |
| 220 | 365 | 5.9 | 33 | 43.7 | 34.5 |

[a]Calculated based on weight of dried washed cells and weight of methanol charged.

In the early stages of the run the fermentation mixture tended to be foamy but after about 80 hours showed no tendency toward foaming. The results showed that NRRL B-15740 gave reasonably good yields growing on methanol substrate and at acceptable cell densities.

EXAMPLE II

Another continuous fermentation run using NRRL B-15740 and methanol substrate was made in the same fermentor utilized in Example I. The same media (see Table II) and methanol concentration of Example I were also employed in this run. In this run a higher initial temperature (37° C.) was employed. Some of the conditions and results are shown in Table IV below.

TABLE IV

| Time hr | Feed mL/hr | pH | Temp. °C. | Yield % | Washed Cells g/L |
|---|---|---|---|---|---|
| 45 | 825 | 6.5 | 37 | 39.3 | 31.1 |
| 95 | 470 | 7.2 | 35 | 40.4 | 31.9 |
| 124 | 470 | 6.5 | 35 | 41.0 | 32.4 |
| 147 | 310 | 6.5 | 30 | 43.3 | 34.0 |

At 147 hr. the run was discontinued because of apparent contamination with other microorganisms. This run showed that NRRL B-15740 was able to grow on methanol at the relatively high temperature of 37° C. with reasonably good yield and at acceptable cell densities.

EXAMPLE III

A further continuous fermentation run using NRRL B-15740 and methanol substrate was made in a 4 liter fermentor equipped as described in Example I. During the run the methanol charged was significantly increased in order to raise cell density. As will be seen in Table V this caused a decrease in cell yield.

TABLE V

| Time hr | Feed mL/hr | pH | Temp. °C. | Yield % | Washed Cells g/L |
|---|---|---|---|---|---|
| 72 | 250 | 6.5 | 33 | 43.6 | 17.2 |
| 96 | 310 | 6.5 | 32 | 44.4 | 17.6 |
| 120 | 310 | 6.5 | 32 | 45.2 | 17.9 |
| 168 | 310$^a$ | 6.1 | 36 | 35.4 | 54.7 |
| 176$^c$ | 400$^b$ | 6.2 | 37 | 27.6 | 65.6 |

$^a$Methanol (undiluted) charged separately from media at a rate of 70 mL/hr; mineral content of the media employed was 2 × that set forth in Table II.
$^b$Methanol (undiluted) charged separately from media at a rate of 120 mL/hr; mineral content of the media employed was 2 × that set forth in Table II.
$^c$Estimated time.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A continuous fermentation process for producing bacterial cells which comprises culturing *Methylomonas sp.* 31A (NRRL B-15740) or a mutant thereof under aerobic aqueous fermentation conditions, in an aqueous ferment comprising a cellular phase and an aqueous extracellular phase, employing effective amounts of assimilable carbon energy substrate, assimilable nitrogen source, water, molecular oxygen, and mineral salts.

2. The process according to claim 1 wherein the mineral salts are maintained in the following amounts in each liter of said aqueous ferment: P 1.3 to 6.5 g, K 1.0 to 4.0 g, Mg 0.4 to 1.6 g, Ca 0.1 to 0.7 g, S 0.5 to 2.6 g, Fe 10 to 80 mg, Zn 5 to 65 mg, Cu 1 to 5 mg, Mn 1 to 65 mg, Co 0.1 to 0.7 mg, Mo 0.2 to 10 mg, and B 0.05 to 0.4 mg.

3. The process according to claim 1 wherein said aqueous fermentation conditions include fermentation temperature in the range of 25° C. to 42° C., pH in the range of 5 to 8, pressure in the range of about 0 to 150 psig, and fermentation time in the range of about 1 to 20 hours based on average retention.

4. The process according to claim 3 wherein a cellular yield of about 40 to 45 grams per 100 grams substrate charged is maintained.

5. The process according to claim 4 wherein said carbon energy substrate is selected from the group consisting of:
methanol,
methylamine,
glucose,
and mixtures of any two or more thereof.

6. The process according to claim 4 wherein said carbon energy substrate is a mixture of
(i) at least one selected from the group consisting of:
methanol,
methylamine, and
glucose; and
(ii) at least one selected from the group consisting of:
formaldehyde and
formate.

7. The process according to claim 5 wherein said carbon energy substrate is methanol.

8. The process according to claim 1 further comprising the steps of:
(a) removing a stream of said aqueous ferment from the fermentation means,
(b) separating said stream of aqueous ferment into a cell-containing fraction, and a separated aqueous media fraction containing residual dissolved minerals,
(c) water-washing said cell-containing fraction, thereby substantially separating traces of said mineral salts from the cells, leaving a wet cell mass,
(d) drying said wet cell mass to produce dried cells, and
(e) recycling the water-washings and separated aqueous media fraction to said culturing to provide therein at least in part the makeup water and said mineral salts.

9. The process according to claim 1 further comprising the steps of:
removing a portion of said aqueous ferment as fermentor effluent containing both a cellular phase and an aqueous extracellular phase including residual mineral salts, and
drying said aqueous ferment effluent containing said cellular phase and said aqueous phase, thereby producing a dried cellular product containing residual water-soluble substances including salts.

10. The process of claim 1 further comprising the steps of:
(a) removing a stream of said aqueous ferment effluent from the fermentation means,
(b) centrifuging said removed aqueous ferment, thereby producing concentrated cells, and a recycle mineral salts aqueous liquor,
(c) water-washing said concentrated cells to produce water-washings containing further residual mineral salts, and washed cells,
(d) drying said washed cells, and
(e) recycling at least a part of at least one of said lean recycle liquor and said water-washings to said aqueous ferment to provide therein at least a portion of makeup water and mineral salts.

11. The process according to claim 2 further employing in said aqueous ferment at least one element selected from the group consisting of sodium and selenium.

12. The process according to claim 2 wherein said mineral salts comprise a primary mineral salts medium and a trace mineral salts medium, and wherein said primary mineral salts medium supplies said P, K, Mg, S, and Ca; and said trace mineral salts medium furnishes said Fe, Zn, Mn, Cu, Co, Mo and B.

13. The process according to claim 1 wherein said carbon energy substrate is selected from the group consisting of methanol, methylamine, glucose, and mixtures of any two or more thereof.

14. The process according to claim 1 wherein said carbon energy substrate is a mixture of
(i) at least one selected from the group consisting of:
methanol,
methylamine, and
glucose; and
(ii) at least one selected from the group consisting of:
formaldehyde and
formate.

15. A method of producing a protein material which comprises culturing a biologically pure culture of the bacterium *Methylomonas Sp.* NRRL B-15740 in an aqueous medium, employing an oxygenated hydrocarbon as carbon energy substrate, aerobic aqueous fermentation conditions, mineral salts, assimilable nitrogen source, and oxygen, and recovering from the resulting single cell microorganisms a protein material.

16. The method according to claim 15 wherein said oxygenated hydrocarbon is methanol or glucose.

17. The method according to claim 15 wherein said oxygenated hydrocarbon is methanol.

18. A biologically pure culture of the strain *Methylomonas sp.* 31A (NRRL B-15740).

* * * * *